(12) United States Patent
Choi et al.

(10) Patent No.: US 10,966,689 B2
(45) Date of Patent: Apr. 6, 2021

(54) METHOD AND APPARATUS FOR PREDICTING CONCENTRATION OF ANALYTE

(71) Applicant: SAMSUNG ELECTRONICS CO., LTD., Suwon-si (KR)

(72) Inventors: Seonmyeong Choi, Suwon-si (KR); Woochang Lee, Anyang-si (KR); June Young Lee, Seongnam-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 144 days.

(21) Appl. No.: 15/590,094

(22) Filed: May 9, 2017

(65) Prior Publication Data

US 2017/0319185 A1    Nov. 9, 2017

(30) Foreign Application Priority Data

May 9, 2016 (KR) ........................ 10-2016-0056569

(51) Int. Cl.
| | | |
|---|---|---|
| *A61B 10/00* | (2006.01) | |
| *G01N 21/359* | (2014.01) | |
| *G01J 3/42* | (2006.01) | |
| *G01J 3/44* | (2006.01) | |
| *A61B 5/1455* | (2006.01) | |
| *G01N 33/483* | (2006.01) | |
| *A61B 5/00* | (2006.01) | |
| *A61B 5/1495* | (2006.01) | |
| *A61B 5/145* | (2006.01) | |
| *G01N 21/35* | (2014.01) | |
| *A61B 5/15* | (2006.01) | |

(52) U.S. Cl.
CPC ........ *A61B 10/0045* (2013.01); *A61B 5/1405* (2013.01); *A61B 5/1455* (2013.01); *A61B 5/1495* (2013.01); *A61B 5/14532* (2013.01); *A61B 5/14546* (2013.01); *A61B 5/7267* (2013.01); *G01J 3/42* (2013.01); *G01J 3/44* (2013.01); *G01N 21/35* (2013.01); *G01N 21/359* (2013.01); *G01N 33/4833* (2013.01); *A61B 2560/0223* (2013.01); *G01N 2201/129* (2013.01)

(58) Field of Classification Search
None
See application file for complete search history.

(56) References Cited

U.S. PATENT DOCUMENTS

| | | | |
|---|---|---|---|
| 7,460,895 | B2 | 12/2008 | Arnold et al. |
| 7,613,487 | B2 | 11/2009 | Shimomura |
| 7,725,144 | B2 | 5/2010 | Ediger et al. |
| 7,787,924 | B2 | 8/2010 | Acosta et al. |
| 7,925,861 | B2 | 4/2011 | Stuttard et al. |
| 7,946,985 | B2 | 5/2011 | Mastrototaro et al. |
| 8,306,766 | B2 | 11/2012 | Mueller, Jr. et al. |
| 8,679,016 | B2 | 3/2014 | Mastrototaro et al. |
| 9,103,793 | B2 | 8/2015 | Bechtel et al. |
| 10,032,270 | B2 | 7/2018 | Turner |
| 2004/0012789 | A1 | 1/2004 | Guthermann |
| 2004/0068163 | A1 | 4/2004 | Ruchti et al. |
| 2006/0167348 | A1 | 7/2006 | Arnold et al. |
| 2006/0173260 | A1 | 8/2006 | Gaoni et al. |
| 2009/0118605 | A1 | 5/2009 | Van Duyne et al. |
| 2011/0168575 | A1 | 7/2011 | Lica et al. |
| 2015/0297144 | A1 | 10/2015 | Kamimura |
| 2016/0283241 | A1 | 9/2016 | Stuttard et al. |

FOREIGN PATENT DOCUMENTS

| | | |
|---|---|---|
| CN | 103876749 | 6/2014 |
| CN | 105492887 | 4/2016 |
| JP | 2006512931 | 4/2006 |
| JP | 5511033 | 6/2014 |
| JP | 5675889 | 2/2015 |
| KR | 1020040020878 | 3/2004 |
| KR | 100883153 | 2/2009 |
| KR | 1020120043189 | 5/2012 |
| KR | 101423851 | 7/2014 |

OTHER PUBLICATIONS

Quora, "When a monochromatic light passes through a prism will it show dispersion?," (https://www.quora.com/When-a-monochromatic-light-passes-through-a-prism-will-it-show-dispersion) downloaded Aug. 12, 2019.*
Quora, "What happens if you shine a laser into a prism?," (https://www.quora.com/What-happens-if-you-shine-a-laser-into-a-prism) downloaded Aug. 12, 2019.*
Wikipedia, "Dispersion (optics)," (https://en.wikipedia.org/wiki/Dispersion_(optics)) downloaded Aug. 12, 2019.*
Wikipedia, "Prism," (https://en.wikipedia.org/wiki/Prism) downloaded Aug. 12, 2019.*
Wikipedia, "Refraction," (https://en.wikipedia.org/wiki/Refraction) downloaded Aug. 12, 2019.*
Olesberg, Jonathon T., et al. "In vivo near-infrared spectroscopy of rat skin tissue with varying blood glucose levels." Analytical chemistry 78.1 (2006): 215-223.*
European Search Report—European Patent Application No. 17168232.1 dated Oct. 4, 2017.
Japanese Office Action—Japanese Patent Application No. 2017-090491 dated Dec. 15, 2020, citing references listed within.
Mark A. Arnold, Ph.D., et al., "Selectivity Assessment of Noninvasive Glucose Measurements Based on Analysis of Multivariate Calibration Vectors", Journal of Diabetes Science and Technology, (Jul. 31, 2007), vol. 1, Issue 4, pp. 454-462.
Chinese Office Action-Chinese Patent Application No. 201710306695.X dated Feb. 2, 2021, citing references listed within.

* cited by examiner

*Primary Examiner* — G Steven Vanni
(74) *Attorney, Agent, or Firm* — Cantor Colburn LLP

(57) ABSTRACT

Disclosed is a method for predicting an in vivo concentration of an analyte, including: estimating an in vivo intrinsic spectrum of the analyte; and predicting the in vivo concentration of the analyte by using a concentration predicting algorithm based on the estimated in vivo intrinsic spectrum and an in vivo spectrum obtained during a section in which the in vivo concentration of the analyte is not substantially changed.

14 Claims, 9 Drawing Sheets

METHOD AND APPARATUS FOR PREDICTING CONCENTRATION OF ANALYTE

CROSS-REFERENCE TO RELATED APPLICATION

This application claims priority to Korean Patent Application No. 10-2016-0056569 filed on May 9, 2016, and all the benefits accruing therefrom under 35 U.S.C. § 119, the content of which in its entirety is herein incorporated by reference.

BACKGROUND

(a) Field

Embodiments of the invention relate to a method and an apparatus for predicting an in vivo concentration of an analyte from a bio-signal.

(b) Description of the Related Art

For predicting an in vivo concentration of an analyte from a bio-signal, a partial least squares ("PLS") algorithm or a net analyte signal ("NAS") algorithm may be employed. Further, after projecting an electromagnetic wave such as an infrared ray or the like to a test subject, an in vivo spectrum obtained as a result of an interaction between an analyte and the electromagnetic wave may be used in the above-stated algorithms for predicting the concentration of the in vivo analyte. In this case, the in vivo spectrum may be obtained by using an optical method such as infra-red spectroscopy, Raman spectroscopy, or the like.

The PLS algorithm is a statistical modeling tool for obtaining a correlation between a multivariate input variable (independent variable) and an output variable (dependent variable) by using data obtained from an experiment or the like. When the PLS algorithm is applied to analysis of the bio-signal, a concentration of an analyte at a certain time may be predicted from the bio-signal by learning a spectral change depending on the concentration of the analyte. The PLS algorithm uses the concentration of the analyte at a plurality of times and spectra obtained at corresponding times thereof to predict the concentration of the analyte from the bio-signal, and it is desired to periodically relearn the spectral change depending on a change of the concentration of the analyte to prevent deterioration of predictability.

The NAS algorithm predicts the concentration of the analyte by learning an intrinsic spectrum of the analyte and a spectrum changing factor irrespective of the concentration of the analyte. When in vivo glucose is the analyte, the spectral changing factor irrespective of the concentration of the analyte in the NAS algorithm may be obtained based on an in vivo spectrum obtained during fasting, and the intrinsic spectrum of the analyte may be obtained from light (an infrared ray, a laser, and the like) passing through a solution of an in vitro analyte. In this case, when the intrinsic spectrum of the analyte that is obtained in vitro is different from the intrinsic spectrum of the in vivo analyte, that is, when the intrinsic spectrum of the analyte is distorted in vivo, performance of the NAS algorithm may deteriorate.

SUMMARY

Embodiments of the invention relate to a method and an apparatus for predicting a concentration of an analyte that finely corrects a signal distorting factor such as noises that may be added while an intrinsic spectrum is obtained.

An embodiment of the invention provides an apparatus for predicting an in vivo concentration of an analyte, the apparatus including: a processor; a memory connected to the processor; and a transceiver connected to the processor, where the processor executes a program stored in the memory to perform: estimating an in vivo intrinsic spectrum of the analyte; and predicting the in vivo concentration of the analyte by using a concentration predicting algorithm based on the estimated in vivo intrinsic spectrum and an in vivo spectrum obtained in a section in which the in vivo concentration of the analyte is not substantially changed.

In an embodiment, while the processor may perform the estimating the in vivo intrinsic spectrum of the analyte by obtaining an in vitro intrinsic spectrum of the analyte by using a solution of the analyte, and estimating the in vivo intrinsic spectrum of the analyte by correcting the obtained in vitro intrinsic spectrum.

In an embodiment, the processor may perform the correcting the in vitro intrinsic spectrum by estimating the in vitro intrinsic spectrum based on a linear combination of the in vitro intrinsic spectrum, a constant function term, and a linear function term.

In an embodiment, the processor may perform the predicting the in vivo concentration of the analyte by generating a basis set including at least one principal component of the in vivo spectrum; and predicting the in vivo concentration of the analyte by performing a least squares method using an additional basis set, which is obtained while estimating the in vivo intrinsic spectrum, the basis set including the principal component of the in vivo spectrum, and the estimated in vivo intrinsic spectrum.

In an embodiment, the analyte may be included in one of a human, an animal, a mammal, a non-mammal, and a microorganism.

In an embodiment, the analyte may be at least one of glucose, urea, lactate, triglyceride, protein, cholesterol, and ethanol.

In an embodiment, the analyte may be glucose, and the section in which the concentration of the analyte may not be substantially changed is a fasting section.

In an embodiment, the in vivo spectrum may be one of an absorption spectrum and a reflection spectrum of infra-red light.

In an embodiment, the in vivo spectrum may be a dispersion spectrum obtained by radiating a single wavelength electromagnetic wave to a living body.

In an embodiment, the concentration predicting algorithm may be a net analyte signal ("NAS") algorithm.

Another embodiment of the invention provides a method for predicting an in vivo concentration of an analyte, the method including: estimating an in vivo intrinsic spectrum of the analyte; and predicting the in vivo concentration of the analyte by using a concentration predicting algorithm based on the estimated in vivo intrinsic spectrum and an in vivo spectrum obtained during a section in which the in vivo concentration of the analyte is not substantially changed.

In an embodiment, the estimating the in vivo intrinsic spectrum may include: obtaining an in vitro intrinsic spectrum of the analyte by using a solution of the analyte; and estimating the in vivo intrinsic spectrum of the analyte by correcting the obtained in vitro intrinsic spectrum.

In an embodiment, the estimating the in vivo intrinsic spectrum of the analyte by correcting the in vitro intrinsic spectrum may include estimating the in vitro intrinsic spectrum based on a linear combination of the in vitro intrinsic spectrum, a constant function term, and a linear function term.

In an embodiment, the predicting the in vivo concentration of the analyte may include: generating a basis set including at least one principal component of the in vivo spectrum; and predicting the in vivo concentration of the analyte by performing a least squares method using an additional basis set, which is obtained while estimating the in vivo intrinsic spectrum, the basis set including the principal component of the in vivo spectrum, and the estimated in vivo intrinsic spectrum.

In an embodiment, the analyte may be included in one of a human, an animal, a mammal, a non-mammal, and a microorganism.

In an embodiment, the analyte may be at least one of glucose, urea, lactate, triglyceride, protein, cholesterol, and ethanol.

In an embodiment, the analyte may be glucose, and the section in which the concentration of the analyte is not substantially changed may be a fasting section.

In an embodiment, the in vivo spectrum may be one of an absorption spectrum and a reflection spectrum of infra-red.

In an embodiment, the in vivo spectrum may be a dispersion spectrum obtained by radiating a single wavelength electromagnetic wave to a living body.

In an embodiment, the concentration predicting algorithm may be an NAS algorithm.

According to embodiments of the invention, an in vivo concentration of an analyte is accurately predicted by correcting a distortion of an in vivo intrinsic spectrum of the analyte to improve performance of the NAS algorithm.

BRIEF DESCRIPTION OF THE DRAWINGS

These and/or other features of the invention will become apparent and more readily appreciated from the following detailed description of embodiments thereof, taken in conjunction with the accompanying drawings, in which.

DETAILED DESCRIPTION

Figure 1:
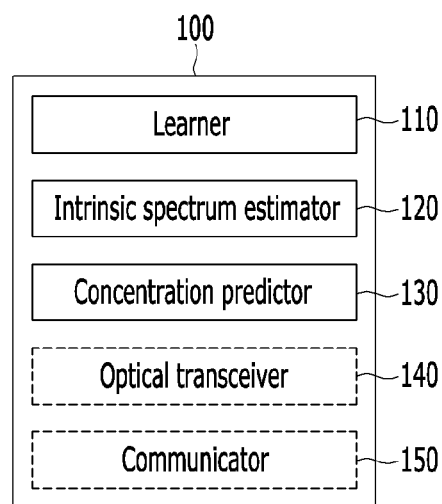
FIG. 1 illustrates a block diagram showing an apparatus for predicting a concentration of an analyte according to an exemplary embodiment of the invention.

Hereinafter, the invention will be described in detail with reference to the accompanying drawings, in which exemplary embodiments of the invention are shown. As those skilled in the art would realize, the described embodiments may be modified in various different ways, all without departing from the spirit or scope of the invention. Accordingly, the drawings and description are to be regarded as illustrative in nature and not restrictive. Like reference numerals designate like elements throughout the specification.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, exemplary embodiments of the invention will be described in detail with reference to the accompanying drawings.

Figure 2:
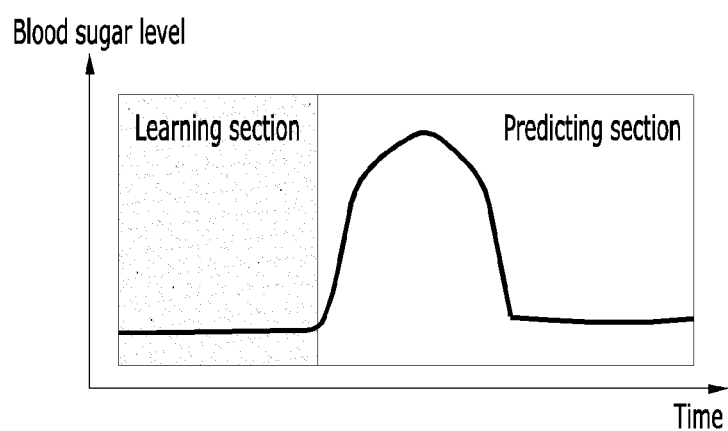
FIG. 2 illustrates a graph for explaining a net analyte signal ("NAS") algorithm according to an exemplary embodiment of the invention.

FIG. 1 illustrates a block diagram of an apparatus for predicting a concentration of an analyte according to an exemplary embodiment of the invention, and FIG. 2 illustrates a graph for explaining a net analyte signal ("NAS") algorithm according to an exemplary embodiment of the invention.

An exemplary embodiment of a concentration predicting apparatus 100 may predict a concentration of an analyte by analyzing an in vivo spectrum using an analyte concentration predicting algorithm. In such an embodiment, after an infrared ray or a laser transmits through (e.g., diffuses and reflects on) a living body, as the infrared ray or the laser is absorbed in or scattered on the analyte, the in vivo spectrum may be obtained, and the in vivo spectrum may be continually obtained according a predetermined time interval. The in vivo spectrum may be obtained by infra-red spectroscopy, Raman spectroscopy, or the like to be applied to the concentration predicting algorithm.

An exemplary embodiment of the concentration predicting apparatus 100 may use the NAS algorithm as an algorithm for predicting an in vivo concentration of an analyte, as shown in FIG. 2, which is an explanatory schematic view of the NAS algorithm according to an exemplary embodiment of the invention. In such an embodiment, the NAS algorithm may predict the concentration of the in vivo analyte during a predicting section based on a principal component spectrum of the in vivo spectrum obtained during a learning section and an intrinsic spectrum of the analyte that is separately obtained in vitro. In such an embodiment, the learning section may be a section in which an in vivo blood sugar level is not substantially changed. For the NAS algorithm, the intrinsic spectrum of the analyte that is experimentally obtained in vitro may be obtained by sensing light passing through a solution of the analyte.

In an exemplary embodiment, the concentration predicting apparatus 100 may predict an in vivo concentration of an analyte of each of humans, animals, mammals, non-mammals, and microorganisms. The in vivo analyte may be at least one of glucose, urea, lactate, triglyceride, protein, cholesterol, and ethanol. Hereinafter, for convenience of description, an exemplary embodiment, where an analyte for the concentration predicting apparatus 100 is the glucose and the concentration predicting apparatus 100 predicts an in vivo blood sugar level, will be described in detail, but not being limited thereto. In an alternative exemplary embodiment, a concentration of a material other than the above listed analytes may also be predicted by the concentration predicting apparatus 100.

In an exemplary embodiment, the concentration predicting apparatus 100 may include or operate through a processor, a memory and a transceiver. The memory may be connected to the processor to store various information for driving the processor. The transceiver may be connected to the processor to transmit and receive wired or wireless signals to and from a terminal, a server, or the like. The processor may be configured to implement a function, a process, or a method for predicting a concentration. In an exemplary embodiment, an operation of the concentration predicting apparatus may be implemented by the processor.

In an exemplary embodiment of the invention, the memory may be disposed at an interior or exterior of the processor, and may be connected to the processor by a means or an element that is well-known in the art. The memory may be one of various volatile and non-volatile storage media or device. In one exemplary embodiment, for example, the memory may include a read-only memory ("ROM") or a random access memory ("RAM").

In an exemplary embodiment, where the in vivo analyte is glucose, the concentration of the analyte may read blood sugar level, a fasting section may correspond to a section in which the concentration of the analyte is substantially constant, and near infra-red ("NIR") or middle infra-red ("MIR") may be used to obtain the in vivo spectrum.

Referring to FIG. 1, an exemplary embodiment of the concentration predicting apparatus 100 includes a learner 110, an intrinsic spectrum estimator 120, and a concentration predictor 130. In such an embodiment, each of the learner 110, the intrinsic spectrum estimator 120, and the concentration predictor 130 may be implemented using a processor, e.g., an instruction implemented in a processor.

The learner 110 learns a spectral change factor irrespective or independent of a concentration change of the analyte based on a fasting spectrum during the learning section. In such an embodiment, the learner 110 may learn the spectral change factor irrespective or independent of the concentration change of the analyte by using principal component analysis ("PCA").

According to an exemplary embodiment, where the analyte is glucose, a plurality of fasting spectra obtained during the learning section may be approximately represented based on a combination of principal component spectra obtained through the principal component analysis on the fasting spectrum. In such an embodiment, the principal component spectrum may represent in vivo spectral change factors other than the blood sugar level, and other component spectra, e.g., n relatively dominant principal component spectra, may be grouped as a basis set. Here, n is a natural number.

The intrinsic spectrum estimator 120 estimates the in vivo intrinsic spectrum by using an intrinsic spectrum of the analyte (hereinafter referred to as 'in vitro intrinsic spectrum') obtained from a correction term and a solution (i.e., in vitro) so that an intrinsic spectrum of the analyte in skin (hereinafter referred to as 'in vivo intrinsic spectrum') may be accurately represented. In the intrinsic spectrum estimator 120, a method for estimating the in vivo intrinsic spectrum uses Equation 1 below. Hereinafter, an exemplary embodiment, where the analyte is glucose and Equation 1 is used, will be described in detail. In such an embodiment, an in vivo intrinsic spectrum $f_{glu,skin}(\omega)$ of the glucose may be obtained using Equation 1 below.

$$f_{glu,skin}(\omega)=a(\omega)(f_{glu,exp}(\omega)+b(\omega))+c(\omega) \quad \text{(Equation 1)}$$

In Equation 1, $f_{glu,exp}(\omega)$ denotes an in vitro intrinsic spectrum obtained from a glucose solution, and $a(\omega)$, $b(\omega)$ and $c(\omega)$ denote correction terms for correcting the in vitro intrinsic spectrum, respectively. In such an embodiment, the in vivo intrinsic spectrum $f_{glu,skin}(\omega)$ may be represented using correction terms, such as $a(\omega)$, $b(\omega)$ and $c(\omega)$, based on the in vitro intrinsic spectrum $f_{glu,exp}(\omega)$ of the glucose as shown in Equation 1.

Figure 3:
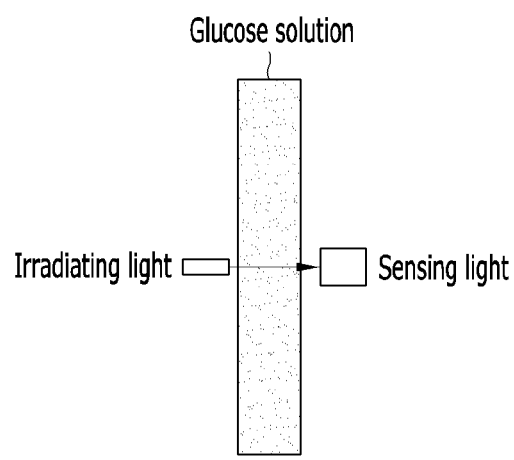
FIG. 3 illustrates a schematic view of a method for obtaining a spectrum for a glucose solution according to an exemplary embodiment of the invention.

In such an embodiment, the in vitro intrinsic spectrum $f_{glu,exp}(\omega)$ of the glucose dissolved in the solution may be experimentally obtained. In an exemplary embodiment, as shown in FIG. 3, the in vitro intrinsic spectrum $f_{glu,exp}(\omega)$ may be obtained by sensing light passed through the glucose solution. In such an embodiment, an optical transceiver 140 for irradiating and receiving light to and from an in vivo body may be disposed outside the concentration predicting apparatus, and the concentration predicting apparatus 100 may further include a communicator 150 that may obtain spectra through a wired or wireless communication network from the optical transceiver 140. The communicator 150 may transmit a prediction result of the concentration of the analyte to the outside of the concentration predicting apparatus 100 through the wired or wireless communication. In an alternative exemplary embodiment, a concentration predicting apparatus 100 may further include the optical transceiver 140 to directly obtain the in vivo spectrum.

Figure 4:
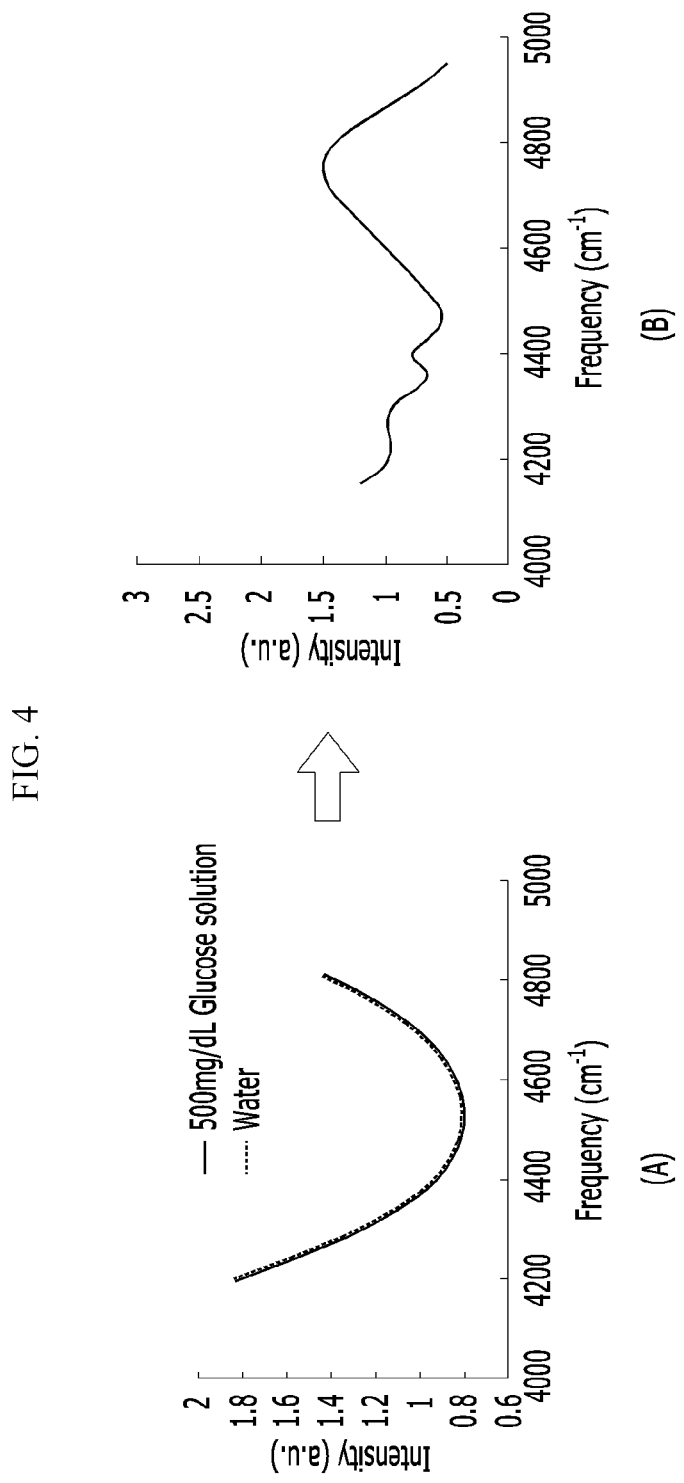
FIG. 4 illustrates graphs showing spectrums of water and a glucose solution for baseline-fitting and a graph of an intrinsic spectrum of glucose obtained through the baseline-fitting, according to an exemplary embodiment of the invention.

FIG. 4 illustrates graphs of spectra of water and a glucose solution for baseline-fitting and a graph of an intrinsic spectrum of glucose obtained through the baseline-fitting, according to an exemplary embodiment of the invention.

Referring to FIG. 4, in an exemplary embodiment, the baseline-fitting is performed between the spectra of the water and the glucose solution to obtain the in vitro intrinsic spectrum of the glucose from the glucose solution. In such an embodiment, the in vitro intrinsic spectrum of glucose is obtained based on a difference between the spectra of the water and the glucose solution. In such an embodiment, several signals included in the in vitro intrinsic spectrum of glucose may be desired to be filtered or removed during a process of the baseline fitting. The in vivo intrinsic spectrum may be distorted due to various factors such as a spectrum obtaining mode (reflection or transmission) of the optical transceiver 140, characteristics of related devices, temperatures of the related devices, noises, amplitude variation of the spectra, etc. Accordingly, concentration prediction accuracy of the NAS algorithm may be improved when the in vivo intrinsic spectrum of the glucose is finely estimated.

In an exemplary embodiment, $a(\omega)$, $b(\omega)$ and $c(\omega)$, which are the correction terms of Equation 1, may be approximately represented as Equation 2 based on a Taylor series.

$$a(\omega) = \sum_i a_i \omega^i \cong a_0 + a_1 \omega \quad \text{(Equation 2)}$$

$$b(\omega) = \sum_i b_i \omega^i \cong b_0 + b_1 \omega$$

$$c(\omega) = \sum_i c_i \omega^i \cong c_0 + c_1 \omega$$

When Equation 2 is substituted into Equation 1, Equation 3 may be derived.

$$f_{glu,skin}(\omega) \cong (a_0 + a_1\omega)(f_{glu,exp}(\omega) + b_0 + b_1\omega) + \quad \text{(Equation 3)}$$

$$c_0 + c_1\omega$$

$$\cong a_0 f_{glu,exp}(\omega) + a_1 \omega f_{glu,exp}(\omega) + \beta_0 + \beta_1 \omega$$

In Equation 3, $\alpha_0$ corresponds to $a_0$, $\alpha_1$ corresponds to $a_1$, $\beta_0$ corresponds to $a_0 b_0 + c_0$, $\beta_1$ corresponds to $a_0 b_1 + a_1 b_0 + c_1$, and $\omega^2$ is neglected or omitted.

In Equation 3, if $\alpha_0$ is assumed to be 1 and $\alpha_1$ is assumed to be 0, Equation 3 may be represented as Equation 4.

$$f_{glu,skin}(\omega) \cong f_{glu,exp}(\omega) + \beta_0 + \beta_1 \omega \quad \text{(Equation 4)}$$

That is, the in vivo intrinsic spectrum of glucose $f_{glu,skin}(\omega)$ may be estimated by a linear combination of the in vitro intrinsic spectrum of glucose $f_{glu,exp}(\omega)$, the $\beta_0$ term corresponding to a constant function term, and the $\beta_1 \omega$ term corresponding to a linear function term, as in Equation 4.

Alternatively, Equation 3 may be represented as Equation 5.

$$f_{glu,skin}(\omega) \cong \alpha_0(f_{glu,exp}(\omega) + \alpha\omega f_{glu,exp}(\omega)) + \beta_0 + \beta_1 \omega \quad \text{(Equation 5)}$$

In Equation 5, $\alpha$ may be statistically determined by an experiment. That is, $\alpha$ may be determined by a statistically representative value for a plurality of subjects. In one exemplary embodiment, for example, $\alpha$ is an average value that may properly represent an actual blood sugar level of the subject. As in Equation 5, when $\alpha$ is statistically determined, a basis set for estimating the in vivo intrinsic spectrum of glucose may be three as in Equation 4.

Figure 5:
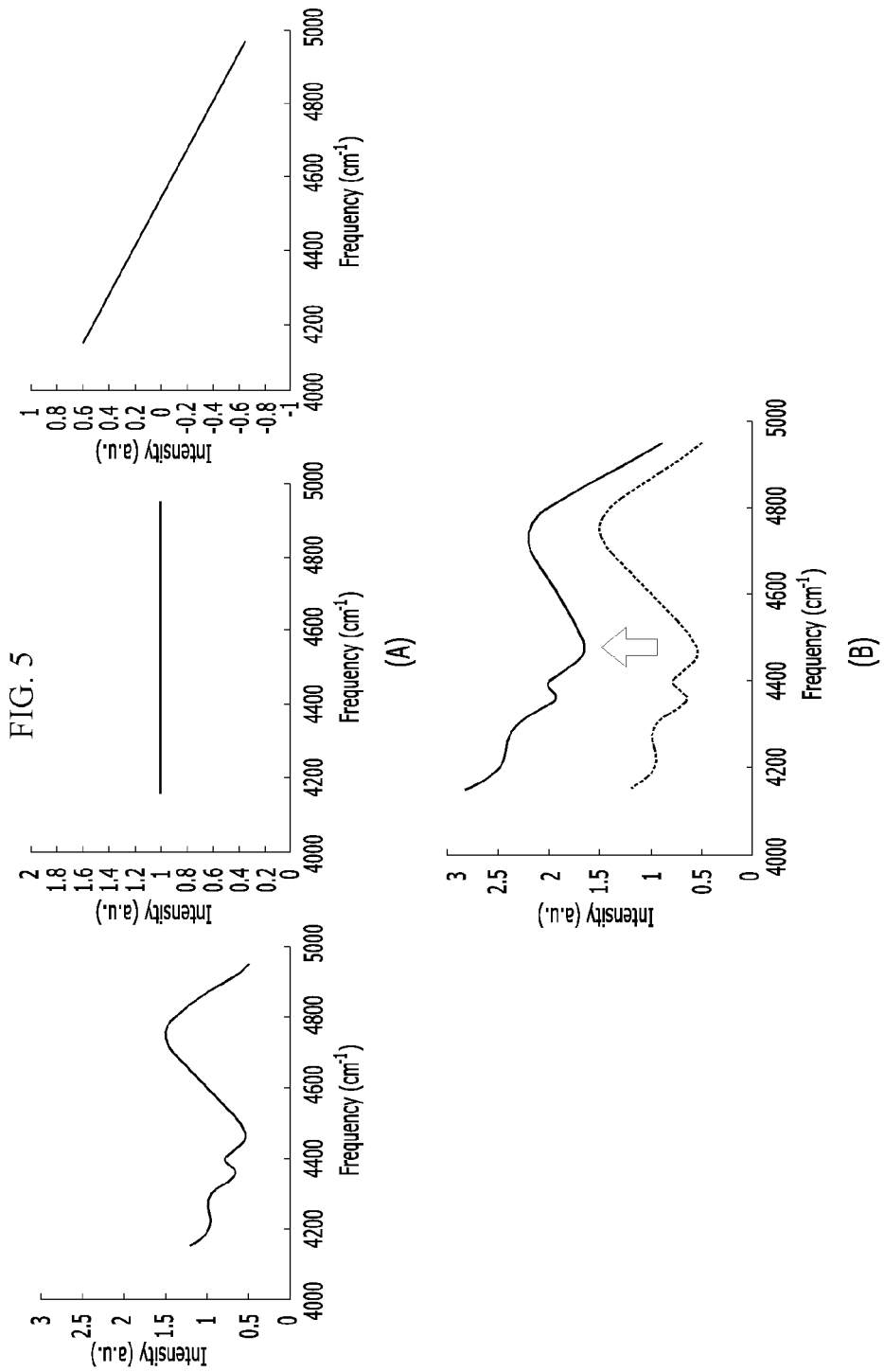
FIG. 5 illustrates graphs showing an in vitro intrinsic spectrum of glucose and a correction term thereof and a graph of an in vivo intrinsic spectrum of glucose, according to an exemplary embodiment of the invention.
Figure 6:
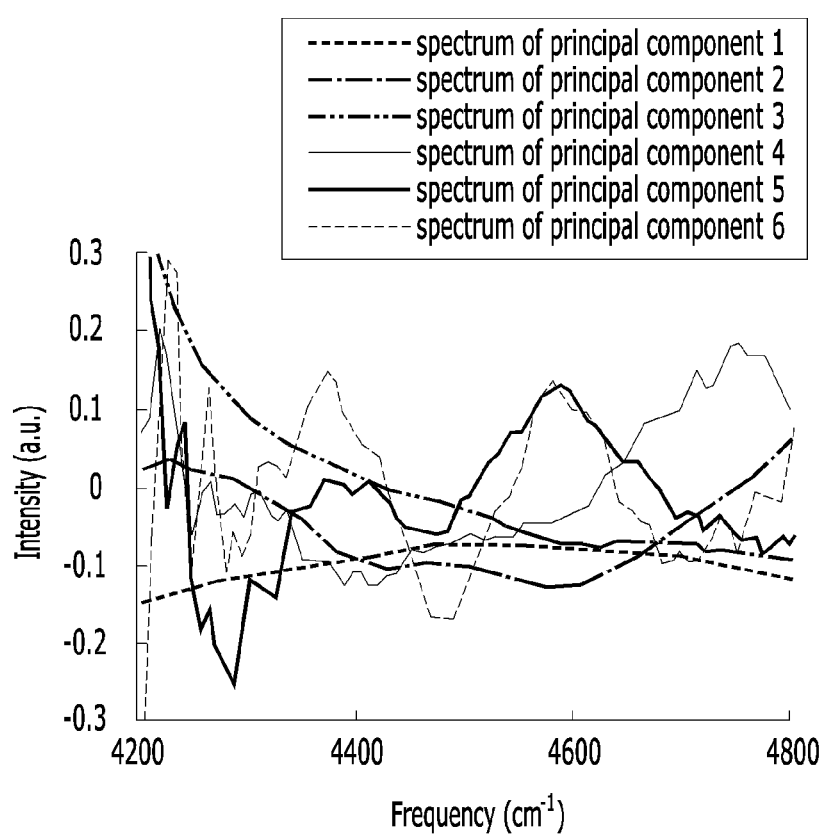
FIG. 6 illustrates a graph showing a basis set of the principal component spectrum with respect to a fasting spectrum according to an exemplary embodiment of the invention.

FIG. 5 illustrates graphs of an in vitro intrinsic spectrum of glucose and a correction term thereof and a graph of an in vivo intrinsic spectrum of glucose, according to an exemplary embodiment of the invention, and FIG. 6 illustrates a graph showing a basis set of the principal component spectrum with respect to a fasting spectrum according to an exemplary embodiment of the invention.

Referring to FIG. 5(A), the in vitro intrinsic spectrum of the glucose obtained from the solution, a graph of the $\beta_0$ term, and a graph of the $\beta_1 \omega$ term are sequentially illustrated from left to right. Referring to FIG. 5(B), the in vitro intrinsic spectrum (shown by a dotted line) of the glucose may be estimated by influence of the $\beta_0$ and $\beta_1 \omega$ terms as shown by a solid line. In an exemplary embodiment, the $\beta_0$ term and the $\beta_1 \omega$ term are an additional basis set that is obtained to improve accuracy of the NAS algorithm.

In an exemplary embodiment, the concentration predictor 130 performs a least squares method based on a basis set (FIG. 6) of the principal component spectrum with respect to the fasting spectrum obtained by the learner 110, the additional basis set obtained by the intrinsic spectrum estimator 120, and the estimated in vivo intrinsic spectrum of the analyte to predict the concentration of the analyte in the predicting section. In an exemplary embodiment, a skin spectrum $f_{skin}(\omega)$ for the NAS algorithm is represented as Equation 6.

$$f_{skin}(\omega) = \sum_i a_i f_{PC,i}(\omega) + a_{glu} f_{glu,skin}(\omega) \quad \text{(Equation 6)}$$

$$\cong \sum_i a_i f_{PC,i}(\omega) + a_{glu} f_{glu,exp}(\omega) +$$

$$a_{glu} \beta_0 + a_{glu} \beta_1 \omega$$

In Equation 6, $f_{PC,i}(\omega)$ denotes the principal component spectrum of the fasting spectrum, and each coefficient of the principal component spectrum denotes a contribution of the skin spectrum $f_{skin}(\omega)$.

The concentration predictor 130 calculates $\alpha_{glu}$, $\beta_0$, and $\beta_1$ by applying the least squares method to Equation 6 representing the skin spectrum. Since the spectrum measured in the learning section does not include a change by the blood sugar level, coefficient $\alpha_i$ of the principal component spectrum (i.e., the basis set of the principal component spectrum) is independent of the blood sugar level. The change of the spectrum by the blood sugar level may be determined by the coefficient $\alpha_{glu}$ of the term of the in vivo intrinsic spectrum of glucose. Accordingly, the concentration of the glucose in the skin may be predicted based on $\alpha_{glu}$ since the concentration $I_{glu}$ of the glucose in the skin is proportional to $\alpha_{glu}$ ($I_{glu} \propto \alpha_{glu}$).

In such an embodiment, the concentration predictor 130 may transmit the predicted result of the concentration of the glucose in the skin, e.g., the blood sugar level, through the communicator 150 to a user, or may display the predicted result of the concentration of the glucose in the skin to the user through an interface included in the concentration predicting apparatus 100. The concentration predicting apparatus 100 may be included in a wearable device and the like, and the measured result of the concentration of the in vivo analyte (e.g., the blood sugar level) obtained by the aforementioned method may be displayed to a user of the wearable device. In one exemplary embodiment, for example, the measured result of the concentration of the in vivo analyte may correspond to a blood sugar level at a desired time, a graph of a blood sugar level change during an inputted period, etc., according to the user's input or instruction.

Figure 7:
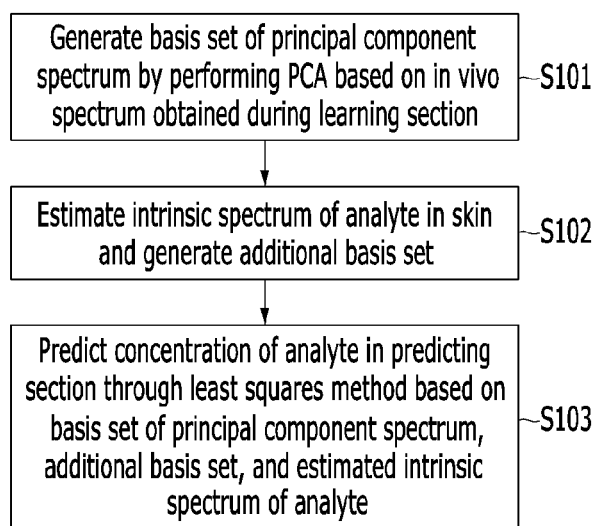
FIG. 7 illustrates a flowchart showing a method of predicting a concentration of an analyte according to an exemplary embodiment of the invention.

FIG. 7 illustrates a flowchart of a method of predicting a concentration of an analyte according to an exemplary embodiment of the invention.

In an exemplary embodiment of a method of predicting a concentration of an analyte, the in vivo spectrum is obtained during the learning section, and the basis set of the principal component spectrum is generated by performing PCA based on the obtained in vivo spectrum (S101). In such an embodiment, the in vivo intrinsic spectrum of the analyte is estimated based on the in vitro intrinsic spectrum and the correction term of the analyte obtained from the solution, and generates the additional basis set (S102). In such an embodiment, the process of estimating the in vivo intrinsic spectrum of the analyte may be the same as those described above with respect to the intrinsic spectrum estimator 120, and any repetitive detailed description thereof will be omitted. In such an embodiment, the least squares method is applied to the basis set obtained from the principal component of the in vivo spectrum during the learning section, the additional basis set obtained during the process of estimating the in vivo intrinsic spectrum of the analyte, and the in vivo intrinsic spectrum of the analyte to calculate the coefficients of the in vivo intrinsic spectrum of the analyte, thereby predicting the in vivo concentration of the analyte during the predicting section (S103).

Figure 8:
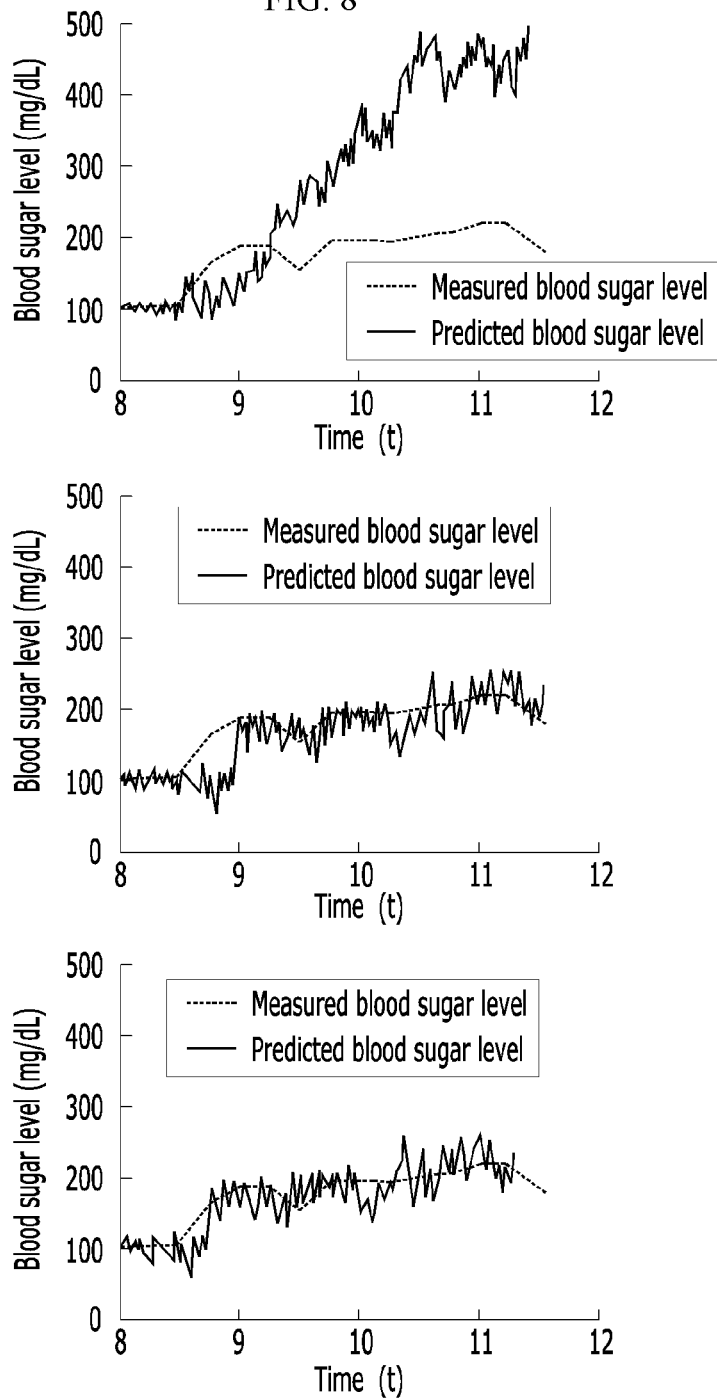
FIG. 8 illustrates graphs for comparing performance of NAS algorithms intended for a human body according to an exemplary embodiment of the invention.

FIG. 8 illustrates graphs for comparing performance of NAS algorithms intended for a human body according to an exemplary embodiment of the invention.

Referring to FIG. 8, the first graph from the top is a graph in which a predicted blood sugar level and a measured blood sugar level are compared based on an in vivo intrinsic spectrum that is not corrected (i.e., based on a conventional NAS algorithm), the second graph from the top is a graph in which the predicted blood sugar level and the measured blood sugar level are compared based on a corrected in vivo intrinsic spectrum (i.e., based on an improved NAS algorithm), and the third graph from the top is a result graph in a state in which a delay time of about 15 minutes is applied to the improved NAS algorithm. Since there is a typical delay time of about 15 minutes between the glucose concentration in the skin and the blood sugar level, the lower graph is a form in which the delay time of about 15 minutes is added to the second graph from the top.

Comparing the first graph and the third graph from the top in FIG. 8, there is a great difference between the predicted result of the blood sugar level using a conventional NSA algorithm and the actually measured blood sugar level after 8:30 since the correction term is not considered in the in vivo intrinsic spectrum. However, in an exemplary embodiment of the invention, the predicted blood sugar level using the improved NAS algorithm based on the finely estimated in vivo intrinsic spectrum is substantially similar to the measured blood sugar level.

Figure 9:
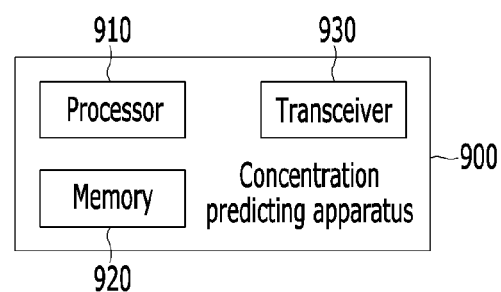
FIG. 9 illustrates a block diagram of an apparatus for predicting a concentration of an analyte according to an exemplary embodiment of the invention.

FIG. 9 illustrates a block diagram of an apparatus for predicting a concentration of an analyte according to an exemplary embodiment of the invention.

Referring to FIG. 9, an exemplary embodiment of a concentration predicting apparatus 900 includes a processor 910, a memory 920, and a transceiver 930.

The memory 920 may be connected to the processor 910 and store various information for driving the processor 910 or a program to be executed by the processor 910. The transceiver 930 may be connected to the processor 910, and may transmit and receive a wired or wireless signal to and from an outside of the concentration predicting apparatus 900. The processor 910 may be configured to implement a function, a process, an instruction, or a method corresponding to the exemplary embodiments of a method of predicting a concentration of an analyte according to the invention as set forth herein. In such an embodiment, operations of the concentration predicting apparatus 900 may be implemented by the processor 910.

In an exemplary embodiment of the invention, the memory may be disposed at an interior or exterior of the processor, and may be connected to the processor by a means or an element well-known in the art. The memory may be one of various volatile and non-volatile storage media or device. In one exemplary embodiment, for example, the memory may include a ROM or a RAM.

While the invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for predicting an in vivo concentration of an analyte, the apparatus comprising:
   a processor and
   a memory connected to the processor, wherein the memory stores a program,
   wherein the program is configured to cause the processor to perform;
   estimating an in vivo intrinsic spectrum of the analyte by correcting an in vitro intrinsic spectrum of the analyte using a linear combination of the in vitro intrinsic spectrum, a constant function term, and a linear function term, wherein the in vitro intrinsic spectrum of the analyte is a spectrum of the analyte itself obtained from a sample comprised of the analyte dissolved in an aqueous buffer solution and
   predicting the in vivo concentration of the analyte by using a net analyte signal based on the estimated in vivo intrinsic spectrum and an in vivo spectrum obtained in a section which is a time duration during which the in vivo concentration of the analyte is not substantially changed.

2. The apparatus of claim 1, wherein
   the processor performs the predicting the in vivo concentration of the analyte by generating a first basis set including a principal component of the in vivo spectrum obtained in the section and by performing a least squares method using a second basis set which is obtained while estimating the in vivo intrinsic spectrum to predict the in vivo concentration of the analyte,
   wherein the first basis set includes the principal component of the in vivo spectrum obtained in the section, and the first basis set further includes the estimated in vivo intrinsic spectrum.

3. The apparatus of claim 1, wherein
   the analyte is in one of a human, an animal, a mammal, a non-mammal, and a microorganism.

4. The apparatus of claim 1, wherein
   the analyte is one of glucose, urea, lactate, triglyceride, protein, cholesterol, and ethanol.

5. The apparatus of claim 1, wherein
   the analyte is glucose, and
   the section in which the concentration of the analyte is not substantially changed is a fasting section.

6. The apparatus of claim 1, wherein
   the in vivo spectrum is one of an absorption spectrum and a reflection spectrum of infra-red light.

7. The apparatus of claim 1, wherein
the in vivo spectrum is a dispersion spectrum, which is a type of spectrum obtained by radiating an infrared ray or a laser to a living body.

8. The method of claim 1, wherein
the analyte is glucose, and
the section in which the concentration of the analyte is not substantially changed is a fasting section.

9. A method for predicting an in vivo concentration of an analyte operated by a processor, the method comprising:
estimating an in vivo intrinsic spectrum of the analyte and
predicting the in vivo concentration of the analyte by using a net analyte signal based on the estimated in vivo intrinsic spectrum and an in vivo spectrum obtained during a section in which the in vivo concentration of the analyte is not substantially changed,
wherein the estimating the in vivo intrinsic spectrum comprises;
obtaining an in vitro intrinsic spectrum of the analyte by using a solution of the analyte, wherein the in vitro intrinsic spectrum of the analyte is a spectrum of the analyte itself obtained from a sample comprised of the analyte dissolved in an aqueous buffer solution and
estimating the in vivo intrinsic spectrum of the analyte by correcting the obtained in vitro intrinsic spectrum, and
wherein the estimating the in vivo intrinsic spectrum of the analyte by correcting the in vitro intrinsic spectrum comprises estimating the in vitro intrinsic spectrum based on a linear combination of the in vitro intrinsic spectrum, a constant function term, and a linear function term.

10. The method of claim 9, wherein
the predicting the in vivo concentration of the analyte comprises;
generating a first basis set including a principal component of the in vivo spectrum obtained during the section and
predicting the in vivo concentration of the analyte by performing a least squares method using a second basis set, which is obtained while estimating the in vivo intrinsic spectrum,
wherein the first basis set includes the principal component of the in vivo spectrum obtained during the section, and the first basis set further includes the estimated in vivo intrinsic spectrum.

11. The method of claim 9, wherein
the analyte is in one of a human, an animal, a mammal, a non-mammal, and a microorganism.

12. The method of claim 9, wherein
the analyte is one of glucose, urea, lactate, triglyceride, protein, cholesterol, and ethanol.

13. The method of claim 9, wherein
the in vivo spectrum is one of an absorption spectrum and a reflection spectrum of infra-red light.

14. The method of claim 9, wherein
the in vivo spectrum is a dispersion spectrum, which is a type of spectrum obtained by radiating an infrared ray or a laser to a living body.

\* \* \* \* \*